United States Patent
Vijfvinkel

(10) Patent No.: US 6,939,341 B2
(45) Date of Patent: Sep. 6, 2005

(54) SURGICAL CUTTING TOOL

(75) Inventor: Gerrit Jan Vijfvinkel, Zuidland (NL)

(73) Assignee: Dutch Opthalmic Research Center (D.O.R.C.), Zuidland (NL)

(*) Notice: Subject to any disclaimer, the term of this patent is extended or adjusted under 35 U.S.C. 154(b) by 0 days.

(21) Appl. No.: 11/023,291

(22) Filed: Dec. 27, 2004

(65) Prior Publication Data

US 2005/0135776 A1   Jun. 23, 2005

Related U.S. Application Data

(63) Continuation of application No. PCT/NL03/00476, filed on Jun. 27, 2003.

(30) Foreign Application Priority Data

Jun. 28, 2002 (NL) .................................. 1020964

(51) Int. Cl.[7] .................. A62B 18/18; A61B 17/32
(52) U.S. Cl. ..................... 606/2; 385/147; 606/170
(58) Field of Search .................. 385/147; 604/22, 604/213; 606/2, 126, 170; 600/178, 179; 83/520

(56) References Cited

U.S. PATENT DOCUMENTS

| | | | |
|---|---|---|---|
| 3,945,375 A | * | 3/1976 | Banko ........................ 600/104 |
| 5,285,795 A | * | 2/1994 | Ryan et al. .................. 600/563 |
| 5,833,643 A | | 11/1998 | Ross et al. .................... 604/22 |
| 6,299,622 B1 | | 10/2001 | Snow et al. ................. 606/159 |
| 6,387,044 B1 | * | 5/2002 | Tachibana et al. .......... 600/114 |

* cited by examiner

*Primary Examiner*—John D. Lee
*Assistant Examiner*—James D. Stein
(74) *Attorney, Agent, or Firm*—Banner & Witcoff, Ltd.

(57) ABSTRACT

This invention provides a cutting tool, comprising a sleeve enclosing a suction chamber where, during use, a reduced pressure prevails and wherein a cutting member is arranged so as to be movable along a suction opening provided in the wall of the sleeve. The wall of the sleeve forms a light conductor. The sleeve can be tubular and is preferably manufactured from light conduction material, in particular glass.

16 Claims, 1 Drawing Sheet

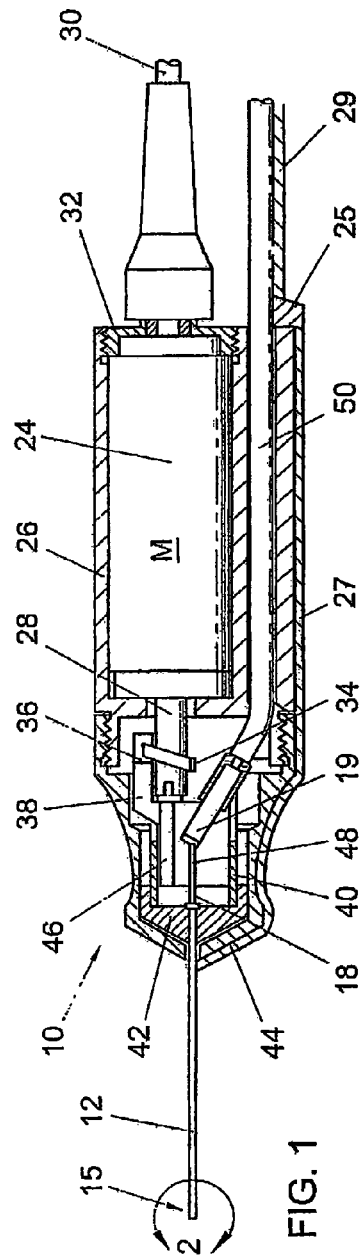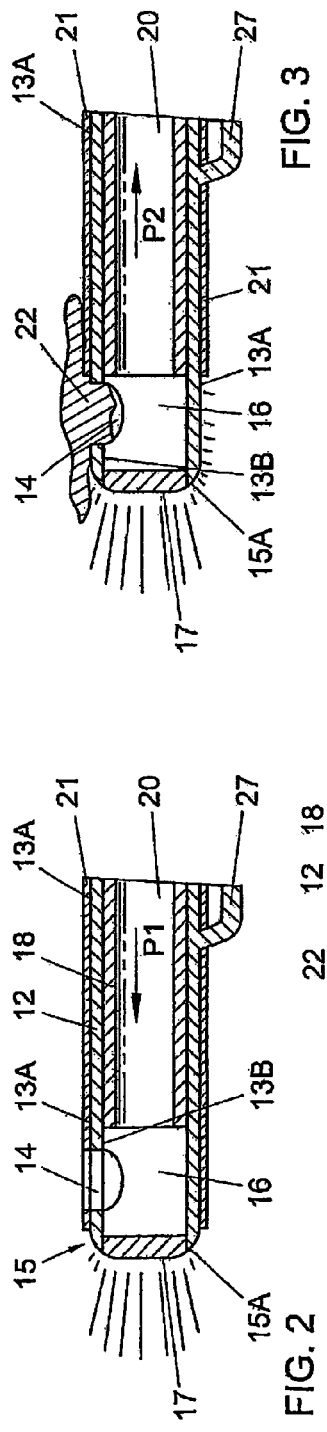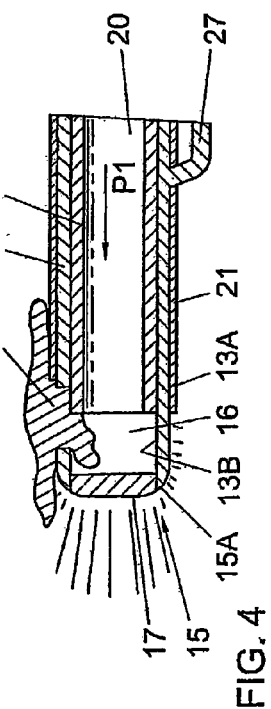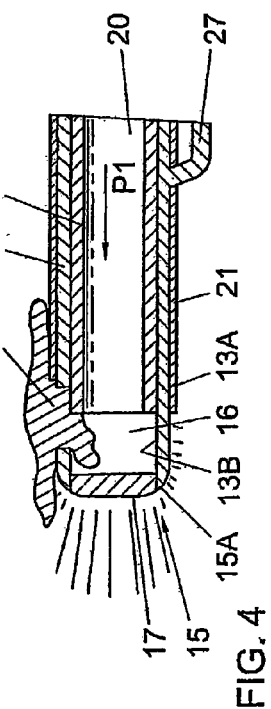

SURGICAL CUTTING TOOL

This application is a continuation of PCT application No. PCT/NL2003/000476, designating the United States and filed Jun. 27, 2003; which claims the benefit of the filing date of Dutch application no. NL 1020964, filed Jun. 28, 2002; both of which are hereby incorporated herein by reference.

The invention relates to a cutting tool, comprising a sleeve enclosing a suction chamber where, during use, a reduced pressure prevails and wherein a cutting member is arranged so as to be movable along a suction opening provided in a wall of the sleeve.

Such a cutting tool is generally known and is used inter alia in surgery for suction, severing by sliding off and draining away of tissue. The surgical variant of the cutting tool is known as a tissue cutter or vitrectome. A tissue cutter suitable for ophthalmic surgery is described in U.S. Pat. No. 5,833,643.

During use, by the suction opening of the sleeve, the cutting tool is contacted with the material to be cut, in surgery: the tissue to be removed. With so-called minimal invasive surgery, the sleeve is then inserted through a narrow incision or opening into a cavity of the patient's body, such as the eye socket or the abdominal cavity, and tissue located in the cavity is contacted with the cutting opening.

During use of the cutting tool, good illumination of the material to be contacted with the cutting opening is of great importance. It is often necessary to then additionally illuminate the material to be operated. In particular with minimal invasive surgery, this is a problem since, for the additional illumination of the operating field, a light source or light conductor needs to be inserted into the body cavity. A drawback of this is that, often, for the insertion of the light source or light conductor, a second incision is necessary. Further, it requires time and effort to bring the light source or light conductor to the operating field, while, furthermore, for handling the light conductor, one hand of the surgeon is occupied.

U.S. Pat. No. 5,285,795 discloses a surgical cutting tool, comprising a sleeve enclosing a suction chamber where, during use, a reduced pressure prevails and wherein in a cutting member is arranged such as to be movable along a cutting opening provided in a wall of the sleeve.

To illuminate the working field, the cutting tool has been provided with a light conductor. The light conductor is formed by a separate glass fiber that is provided onto the sleeve.

To illuminate the working field, the cutting tool has been provided with a light conductor. The light conductor is formed by a separate glass fiber that is provided onto the sleeve.

U.S. Pat. No. 3,945,375 also discloses a surgical cutting tool, comprising a sleeve enclosing a suction chamber where, during use, a reduced pressure prevails and wherein a cutting member is arranged so as to be movable along a suction opening provided in the wall of the sleeve.

Just like the tool according to U.S. Pat. No. 5,285,795, a light conductor has been provided. Again, the light conductor is formed by a separate glass fiber that extends along the sleeve.

In both U.S. Pat. Nos. 5,285,795 and 3,945,375, the illumination function has been provided using a separate element. A problem associated herewith is that the cutting tool has at least at its extremity, a relatively complex geometry that is not only relatively costly to manufacture but also difficult to clean. Further, due to the complex geometry, the risk of damage to the incision is relatively large, which is especially problematic in minimal invasive surgery.

The invention contemplates a cutting tool of the type mentioned in the opening paragraph, in particular a surgical cutting tool for invasive surgery, with which the above-mentioned drawbacks can be avoided. To that end, the invention provides a cutting tool according to the preamble of claim 1 characterized by the features of the characterizing portion of claim 1.

As the wall of the sleeve forms a light conductor, cutting tool and light conductor can be integrated. Illumination of the operating field can thus be carried out in a simple manner, without having to drastically alter the set-up of the cutting tool.

As the wall of the sleeve forms the light conductor, the cutting tool, at least adjacent its extremity, can maintain a relatively simple geometry. Such a simple geometry is not only relatively inexpensive in manufacture, but also easy to clean. Further, the risk of damage to the incision is smaller, which is of advantage specifically with minimal invasive surgery.

Preferably, the sleeve comprises a tube part with a suction opening arranged in the tube wall adjacent an extremity of the tube part, while the tube channel enclosed by the tube wall forms the suction chamber. Such an elongated construction is particularly advantageous as a surgical cutting tool for invasive surgery. Preferably, the cutting member then comprises an inner tube included in the tube channel so as to be coaxially moveable, the inner tube channel of the inner tube being connected to a suction duct during use.

With a cutting tool for ophthalmic surgery, the tube and inner tube can be designed to be capillary tubes.

In an elegant manner, the sleeve is substantially manufactured from light conducting material, preferably from glass. Naturally, the sleeve can also be manufactured from other sorts of light conducting material, such as translucent plastic.

Preferably, the sleeve has an annular, closed cross section, in particular a circular cross section, while the light conducting material forms a continuous ring. Such a sleeve can be manufactured in a very simple manner.

In a further advantageous embodiment, the sleeve is provided with a light exit window located adjacent the suction or cutting opening. Preferably, such a window is designed as a lens so that light transported through the light conductor can exit in a focused beam. Naturally, with the aid of such a window or such a lens, it is also possible to disperse light transported through the light conductor in order to illuminate a larger part of the operating field. In an elegant manner, such a window is situated beyond the suction opening at one extremity of the tube. More in general, the window is preferably located in the operating direction in front of the suction opening. What is thus achieved is that during use, each time, the area which will be drawn-in can be illuminated. In particular, in an advantageous manner, a lens can be provided in the end face of a tubular sleeve.

By providing the inner and/or outer wall of the sleeve at least partly with a preferably non-translucent covering, light can be prevented from exiting from the tube. Such a covering can be formed, for instance, by a reflecting coating and/or by a refractive surface. Naturally, the covering can also be formed by a tube part, such as the inner tube part and/or an outer tube part to be provided around the tube part.

When the cutting tool is designed as a manual cutting tool, the sleeve can be included in a handle. In the handle, a movement mechanism can for instance be accommodated for moving the cutting member along the suction opening provided in the wall of the sleeve. Further, such a handle can be provided with a connecting plug for connecting the suction duct, which plug is in communication with the suction chamber. Further, the handle can be provided with a connection which is in light-conducting communication with the sleeve for connecting a flexible light conductor for guiding light coming from an external light source from this external light source, via the fiber and the handle and the light conducting sleeve to the light exit opening. Naturally, it is also possible to include a light source in the handle which light source is in light-conducting communication with the light conducting sleeve.

Further advantageous embodiments of the invention are represented in the subclaims.

The invention will be further elucidated with reference to an exemplary embodiment represented in a drawing. In the drawing:

FIG. 1 shows a schematic cross section of a manual cutting tool for ophthalmic surgery;

FIG. 2 shows a schematic cross section of the tip of the cutting tool of FIG. 1 just before the cutting;

FIG. 3 shows a schematic cross section of the tip of FIG. 2 during drawing-in of the tissue; and FIG. 4 shows the tip of FIG. 3 during the cutting of draw-in tissue.

The Figures only involve schematic embodiments of an advantageous embodiment of the invention and are exclusively given by way of non-limitative exemplary embodiment. In the Figures, identical parts are indicated with identical reference numerals.

With reference to FIGS. 1–4, a cutting tool 10 is shown which is designed as a manual cutting tool for ophthalmic surgery. The cutting tool 10 comprises a sleeve 12 enclosing a suction chamber 16 where, during use, a reduced pressure prevails. In the suction chamber 16, a cutting member 18 is arranged such that it is moveable along a suction opening 14 formed in the wall 13 of the sleeve 12. The wall 13 of the sleeve 12 forms a light conductor. The sleeve 12 is of tubular design and is manufactured from light conducting material such as glass. The suction opening 14 is provided in the tube wall 13 adjacent a free extremity 15 of the tube part 12, while the tube channel enclosed by the tube wall 12 forms the suction chamber 16. The cutting member 18 is designed as a coaxially moveable inner tube included in the tube channel 16, whose inner tube channel 20, during use, is connected to a suction duct 50. The tube 12 and the inner tube 18 are designed as capillary tubes. In this example, the sleeve 12 is provided, adjacent the suction opening 14, with a light exit window 17 designed as a lens, so that light transported through the light conductor can exit in a focused beam. The light exit window 17 is located beyond the suction opening 14 at the free end 15 of the sleeve in the end face of the sleeve 12. In this example, the outer wall 13a of the sleeve 12 is provided with a non-translucent covering 21, designed as a coating applied to the outer wall 13a of the sleeve 13 whose surface reflects light exiting through the wall 13 back to the inner wall 13b of the sleeve 12. The coating 21 is represented in different ways in FIG. 2 and FIG.3/FIG.4: in FIG. 2 it extends over a larger part of the sleeve than in FIG. 3 and FIG. 4. In FIGS. 3 and 4 it is shown that as well as from the window 17, some light also exits from the non-covered part of the sleeve 12. Naturally, light exiting can also take place over the entire wall of the sleeve or at least a light conducting part thereof. Then, the light conducting wall parts form the window.

The cutting member 18 designed as inner tube forms a non-translucent covering along the inner wall 13b of the sleeve designed as outer tube. In this exemplary embodiment, the cutting member 18, designed as inner tube, is manufactured from metal, such as corrosion-resistant steel, but, naturally, it can also be manufactured from different material, such as a different metal, a metal alloy or a different type of material, for instance glass.

The sleeve 12 is included in a handle 26. In the handle, a driving mechanism, roughly indicated with reference numeral 24 is accommodated for moving the cutting member 18 along the suction opening 14 provided in the wall 13 of the sleeve 12. The handle 26 is provided with a connecting plug 19 for connecting the suction duct 50, which connection plug 19 is in communication, via the inner tube channel 20, with the suction chamber 16. The handle 26 is further provided with a connecting plug 25 for connecting a flexible light conductor 29 which is connected to an external light source (not shown). Via a light conducting fiber 27, the connecting plug 25 is connected to the light conducting tube 12.

In an elegant manner, the connection 25 can be provided directly onto the light conducting tube 12. When the light conducting tube is made of glass, on the outer wall 13A of the sleeve, for instance a glass connecting bead can be melted-on, in which the flexible light conductor 29 or fiber 27 can be included.

It is not that the light conducting fiber 27 or light conductor 29 and the suction duct 50 can be integrated, for instance by manufacturing the wall of the suction duct 50 from light conducting material. It is further noted that it is also possible to include the light source in the handle 26. By manufacturing the cutting member 18 at least partly from light conducting material, the light conducting sleeve 12 can be connected with the light source via the cutting member 18. With such a construction, the light conducting sleeve 12 can, for instance, be manufactured only partly from light conducting material. In the exemplary embodiment shown, the light can for instance be supplied via the cutting member 18 designed as inner tube and exit adjacent the free extremity 15 of the sleeve 12 designed as outer tube.

During use, light is led from the light source via the light conducting sleeve 12 to the free extremity 15 of the sleeve 12 so that it can exit outwards adjacent the suction opening 14 via the wall 13. The light can exit, for instance, from the casing surface of the free extremity and/or via the window 17 provided in the end face 15A. Optionally, the non-translucent covering 21 can be designed to be partly detachable or slideable, so that the exit of light from the light conducting sleeve 12 can be set at will.

With reference to FIG. 2, it is shown that the cutting member 18 moves towards the suction opening 14 in the direction of the arrow P1. In FIG. 3, it is shown that the cutting member 18 moves back in the direction of the arrow P2, while further in FIG. 3, it is shown that tissue 22 is drawn into the suction chamber 16 via the suction opening 14. Further, in FIG. 4 it is shown that with the aid of the end face 15A of the cutting member 18 the drawn-in tissue 22 is severed by sliding off, in that the cutting member 18 moves back in the direction of the arrow P1. At the end of the stroke, the tissue that was drawn-in through the suction opening 14 will have been completely slid off and be discharged via the inner tube channel and the suction duct 50.

During the cutting, the operating field can be illuminated with the aid of the light exiting from the wall of the sleeve and/or the light exit window, without insertion of a separate light conductor being necessary.

Again referring to FIG. 1, it is shown that the driving mechanism 24 comprises a motor M with a driven rotation shaft 28. The motor is electrically connected to a power source via wires 30 and connecting plug 32. On the driven rotation shaft 28, an oblique disc 34 is provided cooperating with a groove 36 of a sliding part 38. The sliding part 38 is included in a bearing ring 40. The sleeve 13 is included in an inner cap 42 which, with the aid of the sliding part 38, can be moved in a reciprocating manner. The inner cap 44 is covered with the aid of an outer cap 44.

It will be clear that the invention is not limited to the exemplary embodiment described herein. For instance, the driving mechanism can be designed to be pneumatic. In such a case, the cutting tool can simply be manufactured as a disposable product. Also, naturally, for instance the handle with the driving mechanism can be reused. Further, the sleeve can be cup-shaped or conical. Also, the electrical connecting wire can be provided with a light conducting fiber for connecting the light source to the light conducting part of the sleeve during use.

Such variants will be clear to the skilled person and are understood to fall within the scope of the invention as set forth in the following claims.

What is claimed is:

1. A cutting tool comprising a sleeve enclosing a suction chamber where, during use, a reduced pressure prevails and wherein a cutting member is arranged so as to be movable along a suction opening formed in the wall of the sleeve, characterized in that the wall of the sleeve forms a light conductor.

2. A cutting tool according to claim 1, wherein the sleeve comprises a tube part with a cutting opening formed adjacent one extremity of the tube part in the tube wall and wherein the tube channel enclosed by the tube wall forms the suction chamber.

3. A cutting tool according to claim 1, wherein the cutting member comprises an inner tube included in the tube channel so as to be coaxially moveable, the inner tube channel of the inner tube being connected to a suction duct during use.

4. A cutting tool according to claim 3, wherein tube and inner tube are designed as capillaries.

5. A cutting tool according to claim 1, wherein the sleeve is manufactured at least partly from light conducting material.

6. A cutting tool according to claim 1, wherein the sleeve is provided with a light exit window located adjacent the cutting opening.

7. A cutting tool according to claim 6, wherein the light exit window is designed as a lens.

8. A cutting tool according to claim 1, wherein the inner and/or outer wall of the tube is provided, at least partly, with a covering which prevents exit of light from the sleeve.

9. A cutting tool according to claim 8, wherein the covering is formed by a reflective coating for reflecting exiting light back into the tube wall.

10. A cutting tool according to claim 8, wherein the covering is formed by a refractive structure of the surface of the tube wall for reflecting exiting light back.

11. A cutting tool according to claim 8, wherein the covering is formed by a further tube part provided against the inner and/or outer wall of the light conducting sleeve.

12. A cutting tool according to claim 1, wherein the sleeve is included in a handle.

13. A cutting tool according to claim 1, wherein in the handle, a movement mechanism is accommodated for moving the cutting member along the suction opening provided in the wall of the sleeve.

14. A cutting tool according to claim 12, wherein the handle is provided with a connecting plug four connection of the suction duct, which plug is in communication with the suction chamber.

15. A cutting tool according to claim 12, wherein the handle is provided with a connection which is in light conducting communication with the sleeve for the connection of a flexible light conductor.

16. A cutting tool according to claim 5, wherein the light conducting material is glass.

* * * * *